United States Patent
Li et al.

(10) Patent No.: US 9,730,661 B2
(45) Date of Patent: Aug. 15, 2017

(54) MANIFOLD VALVE DEVICE

(75) Inventors: Chun Li, Beijing (CN); Yunxing Liu, Beijing (CN)

(73) Assignee: Beijing DBT Medi-Tech Development Co., Ltd., Beijing (CN)

( * ) Notice: Subject to any disclaimer, the term of this patent is extended or adjusted under 35 U.S.C. 154(b) by 791 days.

(21) Appl. No.: 14/124,623

(22) PCT Filed: Jun. 6, 2012

(86) PCT No.: PCT/CN2012/076505
§ 371 (c)(1),
(2), (4) Date: May 19, 2014

(87) PCT Pub. No.: WO2012/167722
PCT Pub. Date: Dec. 13, 2012

(65) Prior Publication Data
US 2014/0243665 A1  Aug. 28, 2014

(30) Foreign Application Priority Data
Jun. 8, 2011  (CN) .......................... 2011 1 0151762

(51) Int. Cl.
*A61M 5/00* (2006.01)
*A61B 6/00* (2006.01)
(Continued)

(52) U.S. Cl.
CPC ............ *A61B 6/504* (2013.01); *A61M 5/007* (2013.01); *A61M 39/10* (2013.01); *A61M 39/22* (2013.01);
(Continued)

(58) Field of Classification Search
CPC ........ A61B 6/481; A61B 6/504; A61M 39/10; A61M 39/22; A61M 39/223; A61M 5/007;
(Continued)

(56) References Cited

U.S. PATENT DOCUMENTS

2011/0071393 A1*  3/2011  Liu .................. A61B 6/481
600/432

FOREIGN PATENT DOCUMENTS

CN   201135696 Y   10/2008
CN   201356837 Y   12/2009
(Continued)

OTHER PUBLICATIONS

International Search Report for Application No. PCT/CN2012/076505 dated Sep. 13, 2012.
(Continued)

*Primary Examiner* — Jason Flick
(74) *Attorney, Agent, or Firm* — Jenkins, Wilson, Taylor & Hunt, P.A.

(57) ABSTRACT

A triple three-way valve device comprises: a valve body (1) having a distal end and a proximal end, wherein the proximal end of the valve body (1) is connected with a control knob (2) that is radially rotatable relative to the valve body (1); and a valve rod (3) having a distal end and a proximal end, wherein the valve rod (3) is provided within the valve body (1) and is fixedly connected with the control knob (2). The distal end of the valve body (1) is connected with a seat body (4), which is connected with a plurality of liquid passages and a high pressure pipe passage; a selection member (5) provided at the distal end of the valve body (1), wherein, depending on the position of the control knob (2), the selection member (5) selects the communication relationships between the plurality of liquid passages of the seat body (4), the high pressure pipe passage and the valve rod. With the triple three-way valve device, angiocardiography surgery is simplified, and surgery safety and efficiency are improved.

9 Claims, 2 Drawing Sheets

(51) Int. Cl.
  *A61M 39/10* (2006.01)
  *A61M 39/22* (2006.01)
  *F16K 11/074* (2006.01)

(52) U.S. Cl.
  CPC ......... *A61M 39/223* (2013.01); *F16K 11/074* (2013.01); *A61B 6/481* (2013.01); *Y10T 137/86823* (2015.04)

(58) Field of Classification Search
  CPC . F16K 11/02; F16K 11/074; Y10T 137/86823
  USPC ........................................................ 600/432
  See application file for complete search history.

(56) References Cited

FOREIGN PATENT DOCUMENTS

| | | | |
|---|---|---|---|
| CN | WO 2011032514 A1 * | 3/2011 | ............ A61B 6/481 |
| CN | 102218193 A | 10/2011 | |
| CN | 202105313 U | 1/2012 | |
| WO | WO 2011032514 A1 | 3/2011 | |

OTHER PUBLICATIONS

IPRP and Written Opinion for Application No. PCT/CN2012/076505 dated Dec. 10, 2013.

* cited by examiner

MANIFOLD VALVE DEVICE

TECHNICAL FIELD

The invention relates to a medical device, and more particularly to a manifold valve device.

TECHNICAL BACKGROUND

Nowadays, angiography is used to image, diagnose, examine and treat the structure of the cardiovascular. In the process of the angiography, a catheter is inserted into the body of the patient, and a contrast agent is injected into the cardiovascular to be tested. Thus, the region in the patient, having the contrast agent injected, could be imaged by using an X-ray machine. Within the cardiovascular of the patient, as the X-ray passes through the region having the contrast agent, the X-ray is absorbed by the contrast agent. By this way, the image of the contrast agent in the vessel, i.e., the image of the interior of the vessel, could be shown on the screen of an X-ray machine clearly.

Generally, angiography is an essential technology for examining the cardiovascular of the patient. In addition to a tri-ring syringe, a manifold valve switch is also required in the process of the angiography. The manifold valve switch is arranged between the catheter and the tri-ring syringe. Wherein the manifold valve switch is an essential device for switching among a blood-pressure transducer, a saline supply and a contrast agent supply.

FIG. 1 is a schematic view showing a known manifold valve switch. From left to right in FIG. 1, three switches are arranged, wherein the switch No. 1 is connected to the transducer, the switch No. 2 is connected to the saline supply, and the switch No. 3 is connected to the contrast agent supply. The left end of the manifold valve switch is connected to a high pressure pipe, and the right end of the manifold valve switch is connected to a syringe. Generally, in the process of the angiography, the following steps are performed:

Step (1) connecting the saline pipe to the switch No. 2;
Step (2) turning the switch No. 2 to the position A;
Step (3) turning the switch No. 3 to the position B, pulling the syringe back and filling the saline;
Step (4) turning the switch No. 2 to the position B;
Step (5) turning the switch No. 3 to the position A;
Step (6) pushing forward the syringe to exhaust the air in the switch No. 3;
Step (7) connecting the contrast agent pipe to the switch No. 3;
Step (8) turning the switch No. 3 to the position B;
Step (9) turning the switch No. 1 to the position A;
Step (10) pushing the syringe to exhaust the air in the switch No. 1 and connecting the pressure transducer to the switch No. 1;
Step (11) turning the switch No. 1 to the position B;
Step (12) connecting the high pressure pipe to the front end of the manifold valve switch; and
Step (13) pushing the syringe to exhaust the air in the front end of the manifold valve switch and the air in the high pressure pipe, and connecting with the catheter.

Wherein, Steps (1)-(13) are essential operations of exhausting the air in the initial setting.

Step (14) turning the switch No. 1 to the position C, for monitoring the signal of the blood pressure;
Step (15) turning the switch No. 3 to the position A, and pulling the syringe back, for drawing the contrast agent;
Step (16) turning the switch No. 1 to the position B, for protecting the transducer;
Step (17) turning the switch No. 2 to the position B;
Step (18) turning the switch No. 3 to the position B, and pushing the syringe, for injecting the contrast agent;
Step (19) turning the switch No. 1 to the position C, and connecting to the transducer, for monitoring the signal of the blood pressure; and
Step (20) turning the switch No. 3 to the position A, and connecting to the contrast agent supply for filling the contrast agent to be used in the next angiography.

Wherein, Steps (16)-(20) could be repeated for the next injection.

In the steps mentioned above, in the process of the angiography, the operator is required to used the syringe, at the same time, the operator is also required to turn these switches of the manifold valve switching device frequently. Thus, the known manifold valve switch is extremely inconvenient for the operator and might affect the security and the efficiency of the operation. Accordingly, there has grown up an urgent need of a new manifold valve for obviating the problems as mentioned above.

SUMMARY

Accordingly, for substantially obviating one or more disadvantages of the related art, the present disclosure is directed to a manifold valve device comprising: a valve body including a valve body distal end and a valve body proximal end. Said valve body proximal end is connected with a control button capable of being rotated radially relative to said valve body; a valve stem including a valve stem distal end and a valve stem proximal end, wherein said valve stem is provided within said valve body and is fixed to said control button; a pedestal body connected to said valve body distal end and connected to a plurality of fluid passages and a high-pressure pipe passage; a selection component is provided at said valve body distal end. According to the position where said control button is arranged, said selection component is capable of selecting the interconnecting relationships among said plurality of fluid passages, said high pressure pipe passage and said valve stem.

Accordingly, for the manifold valve switch device provided in the present disclosure, by a simple structure, the functional switching among the plurality of fluid passages can be implemented. Thus, the operation of the angiography is significantly simplified, the security and the efficiency of the operation are greatly improved.

BRIEF DESCRIPTION OF THE DRAWINGS

The present disclosure will become more fully understood from the detailed description given herein below for illustration only, and thus are not limitative of the present disclosure, and wherein.

SYMBOL DESCRIPTION

Figure 1:
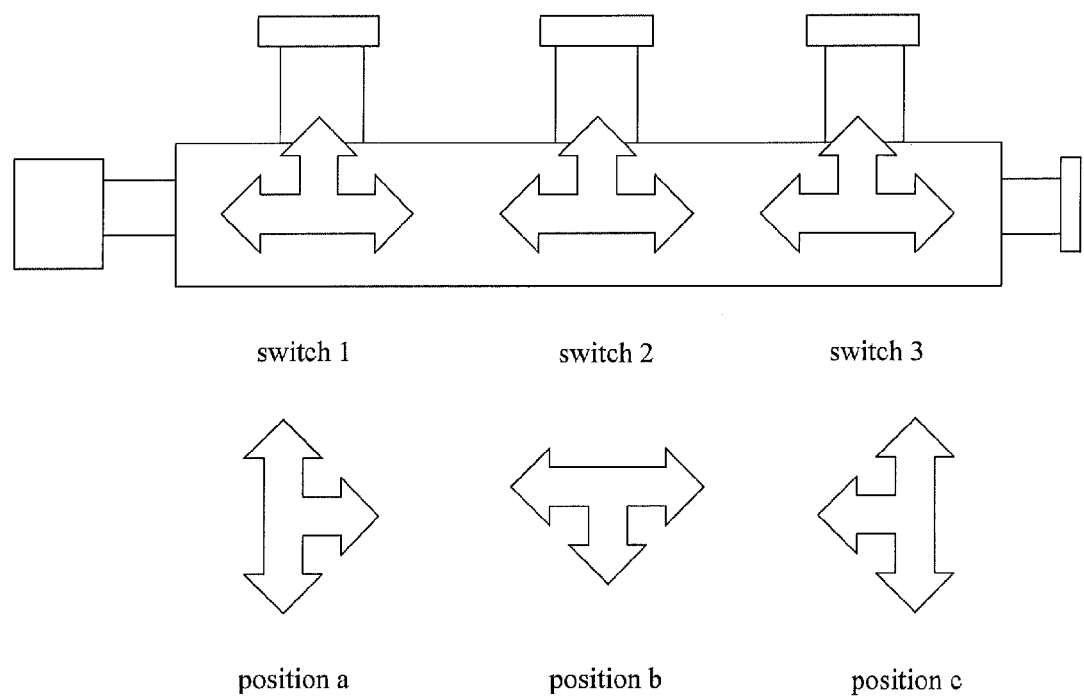
FIG. 1 is a schematic view showing a kwon manifold valve switch.

| | |
|---|---|
| valve body 1 | control button 2 |
| valve stem 3 | pedestal body 4 |

-continued

| selection component 5 | nut 6 |
|---|---|
| first valve plate 51 | second valve plate 52 |
| plugging connector 7 | tri-ring syringe 8 |
| base 9 | connection pegs 10 |

DETAILED DESCRIPTION

To further clarify the aspects, the opinions and the advantages of the present disclosure, a more particular description of this disclosure will be rendered by reference to specific embodiments thereof which are illustrated in the appended drawings.

According to the embodiment of the present disclosure, the invention provides a manifold valve device mainly for implementing angiography.

Figure 2:
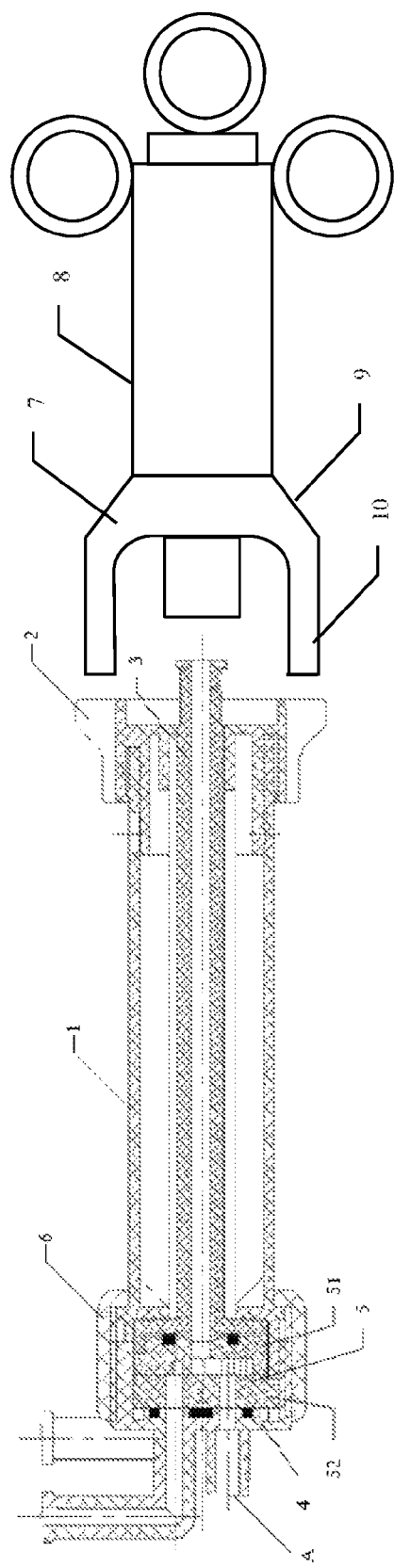
FIG. 2 is a schematic view showing a manifold valve device according to one embodiment of the present disclosure.

FIG. 2 is a schematic view showing a manifold valve device according to one embodiment of the present disclosure. As shown in FIG. 2, the manifold valve device mainly comprises a valve body 1, a control button 2, a valve stem 3, and a pedestal body 4, a selection component 5 and a nut 6.

The valve body 1 is a cylinder body with an interior hollow cavity and includes a distal end and a proximal end. The proximal end of the valve body 1 is connected to the control button 2 which is capable of being rotated radially relative to the valve body 1 but not capable of being rotated axially. In practice, relative to the valve body 1, the control button 2 is configured to be selectively rotated to three positions, i.e., the first position, the second position and the third position. Among these positions, the first position is positioned in the central position and is taken as a starting position. According one embodiment of the present disclosure, the second position is achieved when the control button in the first position is turned counterclockwise by 45 or 90 degrees; the third position can be achieved when the control button in the first position is turned clockwise by 45 or 90 degrees, According to another embodiment of the present disclosure, the second position is achieved when the control button in the first position is turned clockwise by 45 or 90 degrees; the third position can be achieved when the control button in the first position is turned counterclockwise by 45 or 90 degrees. The turned degrees among these positions could be certainly disposed and the degrees will not be limited by the disclosed embodiments. For simplicity, the following description is on the basis of the example that the second position is achieved when the control button in the first position is turned counter-clockwise by 45 or 90 degrees, and the third position is achieved when the control button in the first position is turned clockwise by 45 or 90 degrees.

The valve stem 3 is provided within the valve body 1 and is fixed to the control button 2. Here, the valve stem 3 includes a fluid passage for transmitting the fluid. A distal end and a proximal end extending to the outside of the control button 2 are provided. Thus, relative to the valve body 1, as the control button 2 is radially rotated, the valve stem 3 is capable of being rotated radially together with the control button 2 synchronously. In other words, the valve stem 3 is relatively static to the control button 2.

The distal end of the valve body 1 is connected to the pedestal body 4. Preferably, the pedestal body 4 is capable of being connected to the valve body 1 by a nut. The pedestal body 4 is capable of being connected to a plurality of fluid passages and a high pressure pipe passage. As shown in FIG. 2, the high pressure pipe passage is connect to the opening A of the pedestal body 4. Generally, the plurality of fluid passages includes a transducer passage, a saline passage and a contrast agent passage. One end of the high pressure pipe passage is connected to a catheter which is connected into the patient's body.

Furthermore, a selection component 5 is provided at the distal end of the valve body 1. According to the position where the control button 2 is arranged, the selection component 5 is capable of selecting at least one passage among the transducer passage, the saline passage and the contrast agent passage to connect a selected passage to the valve stem 3, and selection component is capable of connecting or cutting off the communication between the transducer passage and the high pressure pipe passage. Herein, when the control button is arranged at the first position, the selection component 5 is capable of selecting the high pressure pipe passage to connect with the valve stem 3. However the transducer passage, the saline passage and the contrast agent passage are closed down. When the control button 2 is disposed at the second position, the selection component 5 is capable of selecting the transducer passage to connect with the high pressure pipe passage. At this time, only the contrast agent passage can be connected with the valve stem 3 and the saline passage is solely closed down. When the control button 2 is positioned at the third position, the selection component 5 is capable of selecting the transducer passage to connect with the high pressure pipe passage only and the saline passage to connect with the valve stem 3 only. At this time the contrast agent passage is shut down. By only rotating the control button 2, different functional passages can be switched according to actual requirements when performing the angiography.

According to one embodiment of the present disclosure, the selection component 5 includes a first valve plate 51 and a second valve plate 52. The first valve plate 51 is provided on the distal end of the valve body 1 and is fixed to the valve stem 3. The first valve plate 51 is capable of being rotated with the rotation of the valve stem 3 and therefore it can be called as a motive valve plate. The second valve plate 52 is fixed to the pedestal body 4. Thus the second valve plate 52 is relatively fixed when the valve stem 3 is rotated and therefore it can be called as a fixed valve plate. Hence, when the valve stem 3 is rotated, a relative radial rotation realizes between the first valve plate 51 and the second valve plate 52.

During the process of the angiography, it is necessary to have a tri-ring syringe. According one embodiment of the present disclosure, an angiography injection system is provided, and the angiography injection system includes a manifold valve switch device, an inserting connector and a tri-ring syringe.

The specific structure of the manifold valve switch device is given above and will not be described here. As depicted in FIG. 2, the plugging connector 7 is a kind of connecting device used to joint the manifold valve switch device to the tri-ring syringe. The plugging connector 7 includes a base 9 having a hole and a plurality of connection-pegs 10 arranged on the base uniformly. The connection-pegs 10 are fixed to the control button 2 of the manifold valve switch device, wherein the control button has sockets corresponding to the connection-pegs 10. Generally, the number of the connection-pegs is two. The base 9 is fixed to the tri-ring syringe 8. The tri-ring syringe 8 is further capable of connecting with the valve stem 3. Thus, when the tri-ring syringe is rotated, by the plugging connector 7, the rotating moment of the tri-ring syringe is capable of being transmitted to the manifold valve device and thus it is adapted to enable the control button 2 to be rotated with the rotation of the tri-ring syringe 8. Therefore, the operation of the manifold valve device can be controlled only by rotation of the tri-ring syringe.

Specifically, the implementing of the angiography using the manifold valve device according to the invention includes the following specific steps:

Step 1. connecting the saline pipe to the saline passage;

Step 2. turning the control button to the position 3 (i.e., the third position), pulling the syringe back and filling the saline;

Step 3. turning the control button to the position 2 (i.e., the second position);

Step 4. connecting the high pressure pipe passage to the contrast agent passage;

Step 5. pushing the syringe to exhaust the air in the switch from the transducer passage, and then connecting the transducer to the transducer passage;

Step 6. disconnecting the high pressure pipe passage and the contrast agent passage, and connecting the contrast agent pipe to the contrast agent passage;

Step 7. connecting the high pressure pipe passage to the catheter;

Step 8. now the control button is located at the position 2 (i.e., the second position); connecting the transducer to the catheter for monitoring the blood pressure signal; closing the saline passage, connecting the contrast agent passage to the syringe, pulling the syringe back for filling the contrast agent;

Step 9. turning the control button to the position 1, closing the transducer passage for protecting the transducer, connecting the high pressure pipe passage to the valve stem, pushing forward the syringe for injecting the contrast agent and performing the angiography;

Step 10. repeating the Step 8 and Step 9 for preparing the next injection;

Step 11. turning the control button to the position 3, connecting the transducer to the catheter for monitoring the blood pressure signal, closing contrast agent passage, connecting the saline passage to the syringe, pulling the syringe back for filling the saline; and Step 12. turning the control button to the position 1, closing the transducer passage automatically for protecting the transducer, closing the contrast agent passage, connecting the high pressure pipe passage to the syringe, pushing the syringe for injecting saline.

In the embodiment above, the description is on the basis of the example that the second position is achieved when the control button in the first position is turned counter-clockwise by 45 or 90 degrees, and the third position is achieved when the control button in the first position is turned clockwise by 45 or 90 degrees. The embodiments in the invention are not limited to the above embodiment.

The operating steps mentioned indicate that, comparing with the known technologies, the manifold valve device disclosed in the present invention significantly reduces the complexity of the operation and greatly increases the working efficiency.

To sum up, for the manifold valve device provided in the present invention, the switching among the plurality of fluid passages can be implemented by using a simple structure. Thus, the operation of the angiography is significantly simplified, the security and the efficiency of the operation are greatly improved.

The foregoing embodiment is merely exemplary and is not to be construed as limiting the present invention. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A manifold valve device, comprising:
a valve body including a valve body distal end and a valve body proximal end, wherein the valve body proximal end is connected with a control button capable of being rotated radially relative to the valve body;
a valve stem including a valve stem distal end and a valve stem proximal end, wherein the valve stem is provided within the valve body and is fixed to the control button;
a pedestal body connected to the valve body distal end and connected to a plurality of fluid passages and a high-pressure pipe passage;
a selection component provided at the valve body distal end;
a tri-ring syringe; and
a plugging connector, comprising:
a base in which a hole is provided; and
a plurality of connection-pegs uniformly arranged on the base for fixing to the control button,
wherein the base is capable of being fixed to the tri-ring syringe,
wherein, according to the position where the control button is arranged, the selection component is capable of selecting interconnecting relationships among the plurality of fluid passages, the high pressure pipe passage and the valve stem.

2. The manifold valve device according to claim 1, wherein the plurality of fluid passages is three fluid passages, the three fluid passages comprising a transducer passage, a saline passage and a contrast agent passage.

3. The manifold valve device according to claim 2, wherein, according to a position where the control button is arranged, the selection component is capable of selecting the interconnecting relationships among the three fluid passages, the high pressure pipe passage and the valve stem,
wherein as the control button is arranged at a first rotational position, the selection component is capable of selecting the high pressure pipe passage to interconnect with the valve stem, and the transducer passage, the saline passage and the contrast agent passage are closed down;
as the control button is arranged at a second rotational position, the selection component is capable of selecting the contrast agent passage to interconnect with the valve stem and selecting the transducer passage to interconnect with the high pressure pipe passage, and the saline passage is closed down;
as the control button is arranged at a third rotational position, the selection component is capable of selecting the saline passage to interconnect with the valve stem and selecting the transducer passage to interconnect with the high pressure pipe passage, and the contrast agent passage is closed down.

4. The manifold valve device according to claim 3, wherein the second rotational position is 45-90 degrees counter-clockwise from the first rotational position; and the third rotational position is 45-90 degrees clockwise from the first rotational position.

5. The manifold valve device according to claim 3, wherein the second rotational position is 45-90 degrees clockwise from the first rotational position; and the third rotational position is 45-90 degrees counter-clockwise from the first rotational position.

6. The manifold valve device according to claim 1, wherein the selection component includes:
   a first valve plate provided on the valve body distal end and fixed to the valve stem; and
   a second valve plate fixed to the pedestal body,
   wherein the first valve plate is adapted to enable radial rotation relative to the second valve plate.

7. The manifold valve device according to claim 1, further comprising a nut, wherein the valve body is capable of being connected to the pedestal body by the nut.

8. A manifold valve device according to claim 1, wherein the plurality of connection-pegs comprises two connection-pegs.

9. A manifold valve device according to claim 1, wherein the tri-ring syringe is capable of being interconnected with the valve stem, and by the plugging connector, a rotating moment of the tri-ring syringe is capable of being transmitted to the manifold valve device.

\* \* \* \* \*